United States Patent [19]

Saukaitis et al.

[11] Patent Number: 5,430,152

[45] Date of Patent: Jul. 4, 1995

[54] METHOD FOR PREPARING QUINOLINE CARBOXYLIC ACIDS AND DERIVATIVES THEREOF

[75] Inventors: John C. Saukaitis, East Greenwich, R.I.; Franklin B. Gupton, Petersburg, Va.

[73] Assignee: Hoechst Celanese Corporation, Somerville, N.J.

[21] Appl. No.: 180,593

[22] Filed: Jan. 13, 1994

Related U.S. Application Data

[63] Continuation-in-part of Ser. No. 17,583, Feb. 16, 1993, abandoned.

[51] Int. Cl.⁶ .......................................... C07D 215/22
[52] U.S. Cl. ....................................................... 546/153
[58] Field of Search ........................................ 546/153

[56] References Cited

U.S. PATENT DOCUMENTS 4,528,287  7/1985  Itoh et al. ............................ 514/254

OTHER PUBLICATIONS

Hui-Yuan et al, Pharmaceutical Industry, pp. 390–394, 1986.
Bridges et al., J. Heterocyclic Chemistry, vol. 27, pp. 1527–1536, 1990.

*Primary Examiner*—C. Warren Ivy
*Assistant Examiner*—Zinna N. Davis
*Attorney, Agent, or Firm*—Hugh C. Crall

[57] ABSTRACT

A method of preparing substituted and unsubstituted 1,4-dihydro-4-oxo-2 and -3 quinolinic carboxylic acids which comprises heating an ester selected from the group consisting of substituted and unsubstituted anilinomethylenemalonates, anilinofumurates, anilinomaleates and mixutres thereof in the presence of chlorosulfonic acid, oleum and mixtures thereof.

20 Claims, No Drawings

METHOD FOR PREPARING QUINOLINE CARBOXYLIC ACIDS AND DERIVATIVES THEREOF

CROSS-REFERENCE TO RELATED APPLICATIONS

This application is a continuation-in-part of U.S. patent application Ser. No. 08/017,583 filed Feb. 16, 1993, abandoned.

BACKGROUND OF THE INVENTION

1. Technical Field

The invention relates a new method for to the preparation of quinolinic carboxylic acids and derivatives thereof.

2. Background

Heterocyclic compounds of the quinolinic acids are known from the literature. They are intermediates for a broad class of compounds known as quinolones which have antibacterial activity. These compounds were prepared in the late 1930's and the early 1940's by the method of R. G. Gould and W. A. Jacobs, J. Amer. Chem. Soc. 61,2890 (1939). The method consists of the cyclization of diethyl anilinomethylenemalonate derivatives in Dowtherm A, diphenylether at temperatures of 250°–300° C. The starting materials for the cyclization reaction are prepared from a substituted aniline and diethyl ethoxymethylenemalonate. This method has been employed in a number of syntheses, 4,7-Dichloroquinoline, J. Amer. Chem. Soc. 68, 113 (1946); J. Amer. Chem. Soc. 68, 1204 (1946). 6,7 or 8 halo-4-hydroxyquinoline is described in J. Med. Chemistry 21,268 (1978). Other high boiling solvents have been utilized in this reaction as described in German Offenlegungsschrift Nos. 2,343,462 and 2,441,747, U.S. Pat. Nos. 3,149,104 and 3,673,193 and J. Heterocyclic Chem. 21,673 (1984). The use of polyphosphoric acid, sulfuric and acetic acid has been described in J. Org. Chem. Soc. 32, 4155 (1967) and 33, 1218 (1968) and J. Heterocyclic Chem. 27, 1527 (1990). In Pharmaceutical Industry 1986, 17 (9) 390–394, the ring closure of the anilinomethylenemalonate derivative is carried out with various Lewis Acid catalysts namely polyphosphoric ester, polyphosphoric acid, phosphorousoxychloride, phosphorous pentoxide, and a mixture of acetic anhydride and sulfuric acid. The yields obtained with these prior art methods are generally inferior to those of this invention.

A variation on this reaction is the use of anilinomethylenemeldrum's acid esters in place of the normal anilinomethylenemalonic acid esters. These materials are more reactive. However, they are much more expensive to make. Examples of the use of these compounds are given in G. B. Patent 1,147,760; J. Prakt. Chemie. 333, 267 (1990) and J. Heterocyclic Chem. 27, 1527 (1990).

Chloroquine is a quinoline derivative that was found safe for the treatment of plasmodium falciparum malaria in 1946. It was prepared from m-chloroaniline and ethyloxalacetate. The resultant m-chloroanilinomaleate or fumarate derivative was cyclized in diphenylether at high temperature. An industrial procedure is described in Ind. & Eng. Chem (41), 4, 1949, 654–662.

It is advantageous to have a method of preparation that does not utilize Dowtherm A, diphenylether. It is a suspect carcinogen and toxic. High boiling solvents are difficult to separate from the product and generally washing with a low boiling solvent is required to remove the high boiling solvent. In some cases, the addition of a low boiling hydrocarbon solvent is also necessary to precipitate the product from the diphenyl-ether reaction solvent. This situation creates further problems. It is more difficult to recycle the solvent under these conditions. It is advantageous to carry out the reaction in a solvent that can be diluted with water and disposed of without presenting an environmental hazard. It is also an advantage to use inexpensive, readily available starting materials. These and other advantages are achieved by the invention.

Although polyphosphoric, sulfuric, and acetic acid have been found to be effective reaction solvents for the cyclization of certain halogen substituted anilinomethylenemalonates as noted above, they do not provide satisfactory results in the cyclization of trifluoroanilinoacrylic acid esters. The present invention provides an efficient process for preparation of quinolinic acids in high yield by the cyclization of anilinoacrylic acid esters selected from anilinomethylenemalonate, anilinofumurate and anilinomaleate including the trifluoro-substituted derivatives thereof at a moderate temperature without the use of environmentally dangerous, toxic solvents.

SUMMARY OF THE INVENTION

This invention is a process for the preparation of quinolinic acids by the cyclization of anilinomethylenemalonate, anilinofurmate and anilinomaleate esters in a reaction medium comprising chlorosulfonic acid or fuming sulfuric acid (oleum) and mixtures thereof. The cyclization of phenylamino esters takes place with surprising and unexpected ease in the presence of chlorosulfonic acid or fuming sulfuric acid (oleum). The process of the invention is particularly useful for the preparation of trifluoroquinoline carboxylic acids.

The process of the invention is illustrated below:

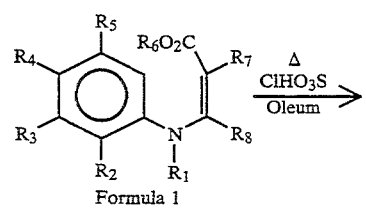

Formula 1

Formula 2

The substituents in the above formulas have the following means:

$R_1$ is hydrogen; $C_1$–$C_5$ alkyl; $C_3$–$C_6$ cycloalkyl; $C_1$–$C_5$ halo-substituted $C_1$ to $C_5$ alkyl wherein halo is F, Cl, Br or I; aryl or $C_1$ to $C_5$ hydroxyalkyl and, $C_1$ to $C_5$ mercaptoalkyl, $R_1$ together with $R_2$ can be joined with an alkylene, oxyalkylene or thioalkylene group to form a 5 or 6 member heterocyclic ring.

R2 is hydrogen, F, Cl, Br, I, $C_1$–$C_5$ alkyl, a halogen substituted $C_1$ to $C_5$ alkyl, $C_1$–$C_5$ alkoxy, $NO_2$—, $R_nN$— wherein R is independently hydrogen or $C_1$ to $C_5$ alkyl and $n=2$; $R_2$ together with $R_1$ can be joined with an alkylene, oxyalkylene or thioalkylene group to form a 5 or 6 member heterocyclic ring.

$R_3$ is hydrogen, F, Cl, Br, I, $C_1$ to $C_4$ alkyl, a halogen substituted $C_1$ to $C_5$ alkyl, $C_1$ to $C_5$ alkoxy, $NO_2$—, or $R_nN$— wherein R is independently hydrogen, or $C_1$-$C_5$ alkyl and $n=2$.

$R_4$ is hydrogen, F, Cl, Br, I, $C_1$ to $C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and $n=2$.

$R_5$ is hydrogen, F, Cl, Br, I, $C_1$-$C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and $n=2$.

$R_6$ is hydrogen, $C_1$-$C_5$ alkyl, $C_3$-$C_6$ cyclo alkyl or phenyl.

$R_7$ is hydrogen, $C_1$-$C_5$ alkyl, alkoxycarbonyl wherein said alkoxy portion is a $C_1$-$C_5$ alkoxy or a $C_2$-$C_6$ cycloalkoxy, a phenoxycarbonyl.

$R_8$ is hydrogen, alkoxycarbonyl, as defined above or phenoxycarbonyl which may be substituted with a halogen or alkyl.

In the process of the invention, the reaction medium comprises chlorosulfonic acid, fuming sulfuric acid (oleum) and mixtures thereof. Fuming sulfuric acid or oleum is a solution of sulfur trioxide in concentrated sulfuric acid. An oleum reaction medium containing 5–30% sulfur trioxide provided excellent results. The reaction medium may be used in an amount equal to about 2 to 10 times the weight of the Formula 1 reactant. The process may be conducted at a temperature of about 40°–180° C., more preferably about 60°–150° C., and most preferably about 70°–90° C.

DESCRIPTION OF THE PREFERRED EMBODIMENTS

This invention is a method for preparing substituted and unsubstituted 1,4-dihydro-4-oxo-2-quinolinic acid and 1,4-dihydro-4-oxo-3-quinolinic acids and derivatives thereof which comprises heating an ester selected from the group consisting of substituted and unsubstituted anilinomethylenemalonates, anilinofumurates and anilinomaleates in the presence of chlorosulfonic acid or fuming sulfuric acid (oleum) and mixtures thereof. The invention provides an efficient environmentally safe process for preparing quinolinic acids in high yield under moderate reaction conditions. These phenylamino esters may be depicted by the following general formula:

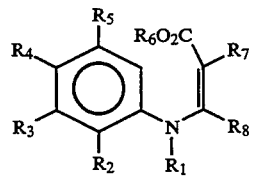

Formula 1

The substituents in the above formulas have the following means:

$R_1$ is hydrogen; $C_1$-$C_5$ alkyl; $C_3$-$C_6$ cycloalkyl; $C_1$-$C_5$ halo-substituted $C_1$ to $C_5$ alkyl wherein halo is F, Cl, Br or I; aryl or $C_1$ to $C_5$ hydroxyalkyl and, $C_1$ to $C_5$ mercaptoalkyl, $R_1$ together with $R_2$ can be joined with an alkylene, oxyalkylene or thioalkylene group to form a 5 or 6 member heterocyclic ring.

$R_2$ is hydrogen, F, Cl, Br, I, $C_1$-$C_5$ alkyl, a halogen substituted $C_1$ to $C_5$ alkyl, $C_1$-$C_5$ alkoxy, $NO_2$—, $R_nN$— wherein R is independently hydrogen or $C_1$ to $C_5$ alkyl and $n=2$; $R_2$ together with $R_1$ can be joined with an alkylene, oxyalkylene or thioalkylene group to form a 5 or 6 member ring.

$R_3$ is hydrogen, halogen (F, Cl, Br, I), $C_1$ to $C_4$ alkyl, a halogen substituted $C_1$ to $C_5$ alkyl, $C_1$ to $C_5$ alkoxy, $NO_2$—, or $R_nN$— wherein R is independently hydrogen, or $C_1$-$C_5$ alkyl and $n=2$.

$R_4$ is hydrogen, F, Cl, Br, I, $C_1$ to $C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and $n=2$.

$R_5$ is hydrogen, F, Cl, Br, I, $C_1$-$C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and $n=2$.

$R_6$ is hydrogen, $C_1$-$C_5$ alkyl, $C_3$-$C_6$ cycloalkyl or phenyl.

$R_7$ is hydrogen, $C_1$-$C_5$ alkyl, alkoxycarbonyl wherein said alkoxy portion is a $C_1$-$C_5$ alkoxy or a $C_2$-$C_6$ cycloalkoxy or, a phenoxycarbonyl.

$R_8$ is hydrogen, alkoxycarbonyl, as defined above or phenoxycarbonyl.

The anilinomethylenemalonate, anilinofumurate and anilinomaleate starting materials may be prepared by known methods; e.g. by the condensation of m-chloroaniline and ethyloxalacetate to produce m-chloroanilinomaleate or fumarate (Ind. & Eng. Chem (41) 4, 1949, 654–662) and by the condensation of a substituted or unsubstituted aniline with diethyl ethoxymethylenemalonate to produce diethyl anilinomethylenemalonate (J. Amer. Chem. Soc. 68, 113 (1946)). The term, "anilino", as used in this description and the claims hereto is intended to include benzoxazinyl and benzothiazinyl moieties Wherein the anilino nitrogen atom and the substituents $R_1$ and $R_2$ have been joined together with an alkylene, oxyalkylene or thioalkylene to form a 5 to 6 member heterocyclic ring.

Exemplary anilinomethylenemalonates are:
diethyl-N-ethyl-,2,3,4-trifluoroanilinomethylenemalonate;
diethyl-N-ethyl-3-chloro-4-fluoroanilinomethylenemalonate;
diethyl-N-ethyl-3,4-difluoroanilinomethylenemalonate;
diethyl-N-(2-fluoroethyl)-2,3,4-trifluoroanilinomethylenemalonate;
diethyl-N-cyclopropyl-3-chloro-4-fluoroanilinomethylenemalonate;
diethyl-N-cyclopropyl-3,4-difluoroaxilinomethylenemalonate;
diethyl-N-cyclopropyl-2,3,4-trifluoroanilinomethylenemalonate;
diethyl-N-(7,8-difluoro-3-methyl-4H-[1,4]benzoxazinyl)methylenemalonate.

Exemplary anilinofumurates are:
diethyl-N-ethyl-,2,3,4-trifluoroanilinofumurate;
diethyl-N-ethyl-3-chloro-4-fluoroanilinofumurate;
diethyl-N-ethyl-3,4-difluoroanilinofumurate;
diethyl-N-(2-fluoroethyl)-2,3,4-trifluoroanilinofumurate;
diethyl-N-cyclopropyl-3-chloro-4-fluoroanilinofumurate;
diethyl-N-cyclopropyl-3,4-difluoroanilinofumurate;

diethyl-N-cyclopropyl-2,3,4-trifluoroanilinofumurate;
diethyl-N-(7,8-difluoro-3-methyl-4H-[1,4]benzoxazinyl)-fumurate.

Exemplary anilinomaleates are:
diethyl-N-ethyl-2,3,4-trifluoroanilinomaleate;
diethyl-N-ethyl-3-chloro-4-fluoroanilinomaleate;
diethyl-N-ethyl-3,4-difluoroanilinomaleate;
diethyl-N-( 2-fluoroethyl)-2,3,4-trifluoroanilinomaleate;
diethyl-N-cyclopropyl-3-chloro-4-fluoroanilinomaleate;
diethyl-N-cyclopropyl-3,4-difluoroanilinomaleate;
diethyl-N-cyclopropyl-2,3,4-trifluoroanilinomaleate;
diethyl-N-(7,8-difluoro-3-methyl-4H-[1,4]benzoxazinyl)-maleate.

Compounds of the general Formula 1 are cyclized in a chlorosulfonic acid or oleum reaction medium to yield substituted and unsubstituted 2-quinolinic and 3-quinolinic acids and derivatives thereof having the following general Formula 2:

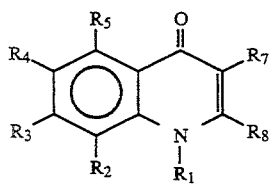

Formula 2

The substituents $R_1$–$R_8$ are defined above with the alcohol, $R_6OH$ being eliminated in the cyclization reaction. A mixed reaction medium comprising chlorosulfonic acid and oleum may be employed in the cyclization reaction.

The ring closure reaction is conducted at a temperature from about 40°–180° C., more preferably about 60°–150° C., most preferably about 70°–90° C. In a preferred embodiment the reaction is conducted at 80° C. The starting material (uncyclized compounds of Formula 1) is heated in a reaction medium comprising chlorosulfonic acid; or fuming sulfuric acid, and mixtures thereof. Optionally a diluent may be present such as nitric acid, phosphoric acid or sulfuric acid or an organic solvent such as acetic acid, acetic anhydride propanoic acid or dichlorobenzene and mixtures thereof. The reaction medium is preferably undiluted chlorosulfonic acid or undiluted oleum. The ratio of chlorosulfonic acid or oleum to the starting material (Formula 1 compound) may be in the range of 2:1 to 10:1. The reaction time will depend upon the ease with which the ring closure is effected. Generally the reaction is carried out over a period of about 5 minutes to about 6 hours, preferably about 0.5 to about 3 hours. The term, "oleum" or "fuming sulfuric acid" as used in this specification is intended to mean a solution of sulfur trioxide in concentrated sulfuric acid. Oleum is a common reagent in the chemical industry being readily available in sulfur trioxide concentrations ranging from 5 to 30 percent.

The reaction time can be determined by simple experimentation. After completion of the reaction period, the desired quinolinic acid may be recovered by simply drowning the reaction mixture in ice water in a weight ratio of 10:1 to 3:1 (water to acid) preferably about 4:1 and filtering the resultant slurry.

The process of the invention may be advantageously used to prepare fluoro-substituted quinoline carboxylic acids which are useful intermediates for the preparation fluorinated quinolone antibacterial compounds (see for example U.S. Pat. No. 4,528,287). Exemplary intermediates which can be prepared according to this invention are:
1-ethyl-1,4-dihydro-4-oxo-6,7,8-trifluoro-3-quinolinic acid;
1-ethyl-1,4-dihydro-4-oxo-6-fluoro-7-chloro-3-quinolinic acid;
1-ethyl-1,4-dihydro-4-oxo-6,7-difluoro-3-quinolinic acids;
1-(2-fluoroethyl)-1,4-dihydro-4-oxo-6,7,8 trifluoroquinolinic acid;
9-10-difluoro-3-methyl-7-oxo-2,3-dihydro-7H-pyrido[1,2,3-de] [1,4]benzoxyazine-6-carboxylic acid;
1-H-1,4 dihydro-4-oxo-6,7,8 trifluoro-3-quinolinic acid;
1-H-1,4-dihydro-4-oxo-6,7,8 trifluoro-2-quinolinic acid;
1-ethyl-1,4-dihydro-4-oxo-5-chloro-6-fluoro-3-quinolinic acid; and
1,4-dihydro-4-oxo-5,7-dichloro-3-quinolinic acid.

The following examples illustrate the invention. These examples are illustrative and not intended to limit the scope of the invention.

EXAMPLES

Example 1

Into a 50 ml 3 neck round bottom flask equipped with a magnetic stirrer and thermal regulator is charged 50 g of chlorosulfonic acid. 12.5 g of diethyl-2,3,4-trifluoroanilinomethylenemalonate is added in portions and the solution heated to 80° C. for 1 hour. The reaction mixture is allowed to cool to 25° C. and then drown into 200 g of ice. The resultant mixture is filtered, washed and dried in a vacuum oven. 9.5 g of 1-H-1,4-dihydro-4-oxo-6,7,8-trifluoro-3-quinolinic acid was obtained after drying, in a 89% yield.

Example 2

The reaction was conducted substantially similar to Example 1 except that 12.5 g of diethyl-N-ethyl-2,3,4-trifluoroanilinomethylenemalonate was utilized along with 50 g of chlorosulfonic acid. 9.5 g of 1-ethyl-1,4-dihydro-4-oxo-6,7,8-trifluoro-3-quinolinic acid was obtained after drowning in ice, filtering, washing and vacuum oven drying, at a 88% yield.

Example 3

The method in Example 1 is followed except that the reaction was run for 2.5 hours. 9.0 g of product were obtained, in a 84% yield.

Example 4

The reaction was run similar to Example 2 except the reaction time was 30 minutes. 9.5 g of product was obtained, in a 88% yield.

Example 5 using a procedure substantially similar to that of Example 1, 9.0 g of diethyl-2,3,4-trifluoroanilinomethylenemalonate were dissolved in 36 g of chlorosulfonic acid. The solution was heated to 80° C. for 2 hours, cooled to 25° C. and drowned into 144 g ice. The product was collected, washed and dried in vacuum oven to yield 6.7 g, 88% yield of 1,4-dihydro-4-oxo-6,7,8-trifluoro-3-quinolinic acid.

Example 6

6.2 g of diethyl-N-ethyl-3-chloro-4-fluoroanilinomethylenemalonate were dissolved in 36 g of chlorosulfonic acid. The reaction mixture was heated to 80° C. for 2 hours, cooled to 25° C. and drowned into 100 g ice. The product was collected, washed, and dried in the vacuum oven to yield 4.9 g, 99% yield of a 60/40 mixture of the two possible isomers, 1-ethyl-1,4-dihydro-4-oxo-5-chloro-6-fluoro-3-quinolinic acid and 1-ethyl-1,4-dihydro-4-oxo-6-fluoro-7-chloro-3-quinolinic- acid.

Example 7

5.7 g of diethyl-N-ethyl-3,4-difluoroanilinomethylenemalonate were treated with 25 g of chlorosulfonic acid in a similar fashion as Example 6. 4.5 g were obtained dry, 94% yield of a 80/20 mixture of the two possible isomers, 1-ethyl-1,4-dihydro-4-oxo-6,7-difluoro-3-quinolinic acid and 1-ethyl-1,4-dihydro-4-oxo-5,6-difluoro-3-quinolinic acid.

Example 8

10.0 g of diethyl-3,5-dichloroanilinomethylenemalonate was added to 40.0 g of chlorosulfonic acid in small portions and the mixture heated to 80° C. over a 30 minute period and heated for 3 additional hours at this temperature. The reaction mixture was cooled to room temperature and drowned into 160 g of ice, filtered and washed. 7.5 g of 1,4-dihydro-4-oxo-5,7-dichloro-3-quinolinic acid were obtained in a 96% yield, after drying in a vacuum oven.

Example 9

10.0 g of diethyl-3,5-dichloroanilinofumurate was treated with 40 g of chlorosulfonic acid in a similar fashion as Example 8. 7.0 g of 1,4-dihydro-4-oxo-5,7-dichloro-2-quinolinic acid was obtained in a 90% yield (dry basis).

Example 10

In a procedure substantially similar to that of Example 5, the diethyl-2,3,4-trifluoroanilino-methylenemalonate was dissolved in sulfuric acid monohydrate and that solution was added to the chlorosulfonic acid reaction medium. The product yield was essentially equivalent to that obtained in Example 5.

Examples 11–16

The following general procedure was used for Examples 11–17. Fuming sulfuric acid (oleum) was the reaction medium. The starting material, 2,3,4-Trifluoro-N-Ethylanilinomethylenemalonate was dissolved in oleum, heated to 80 degrees and held there for 4 hours. The product was analyzed following an ice drown, wash and recovery by vacuum filtration. Reactants, reaction conditions, yield and other specific data are listed for these examples in the following Table I. The reaction product was worked up in all examples by reslurring twice and washing with water three times except in Example 13 where the product was dissolved in sodium hydroxide, filtered and the filtrate reacidified with HCL to recover the product.

TABLE I

| Ex. | Malonate Reactant g | Oleum Amt. g | Oleum $SO_3$ % | Purity | Yld |
|---|---|---|---|---|---|
| 11 | 5.5 | 22.2 | 5 | 69% | 30% |

TABLE I-continued

| Ex. | Malonate Reactant g | Oleum Amt. g | Oleum $SO_3$ % | Purity | Yld |
|---|---|---|---|---|---|
| 12 | 5 | 20 | 10 | 89% | 80%(*) |
| 13 | 5 | 20 | 15 | 93% | 88% |
| 14 | 5 | 20.1 | 20 | 89% | 85% |
| 15 | 5 | 22.8 | 30 | 83% | 71% |
| 16 | 5 | 21.3 | 30 | 89% | 80% |

(*)Yield low due to spillage

Example 17

Example 17 was conducted substantially in accordance with the procedure of Example 16 except the reaction medium was concentrated sulfuric acid. No water insoluble product was formed and the reaction yield was zero.

The invention also may be conducted in a continuous or batch method and may be embodied in other specific forms without departing from the spirit or essential characteristics thereof. Through this specification and the appended claims, a given chemical name or formula is intended encompass all isomers of said name or formula where such isomers exist. The present embodiments are therefore to be considered in all respects as illustrative and not restrictive, the scope of the invention being indicated by the appended claims rather than by the foregoing description; and all changes which come within the meaning and equivalency of the claims are therefore intended to be embraced therein.

We claim:

1. A method of preparing substituted and unsubstituted 1,4-dihydro-4-oxo-2 and -3 quinolinic carboxylic acids which comprises heating an ester selected from the group consisting of substituted and unsubstituted anilinomethylenemalonates, anilinofumurates, anilinomaleates and mixtures thereof in a reaction medium selected from chlorosulfonic acid, oleum and mixtures thereof.

2. A method according to claim 1 wherein said ester has the following formula:

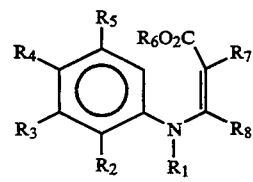

wherein:

$R_1$ is hydrogen; $C_1$–$C_5$ alkyl; $C_3$–$C_6$ cycloalkyl; $C_1$–$C_5$ halo-substituted $C_1$ to $C_5$ alkyl wherein halo is F, Cl, Br or I; aryl or $C_1$ to $C_5$ hydroxyalkyl and, $C_1$ to $C_5$ mercaptoalkyl, $R_1$ together with $R_2$ can be joined with an alkylene, oxyalkylene or thioalkylene group to form a 5 or 6 member heterocyclic ring;

$R_2$ is hydrogen, F, Cl, Br, I, $C_1$–$C_5$ alkyl, a halogen substituted $C_1$ to $C_5$ alkyl, $C_1$–$C_5$ alkoxy, $NO_2$—, $R_nN$— wherein R is independently hydrogen or $C_1$ to $C_5$ alkyl and n=2; $R_2$ together with $R_1$ can be joined with an alkylene, oxyalkylene or thioalkylene group to form a 5 or 6 member heterocyclic ring;

$R_3$ is hydrogen, F, Cl, B, I, $C_1$ to $C_4$ alkyl, a halogen substituted $C_1$ to $C_5$ alkyl, $C_1$ to $C_5$ alkoxy, $NO_2$—, or $R_nN-$ wherein R is independently hydrogen, or $C_1-C_5$ alkyl and n=2;

$R_4$ is hydrogen, F, Cl, B, I, $C_1$ to $C_5$ alkyl a halogen substituted $C_1$ to $C_5$ alkyl, $C_1$ to $C_5$ alkoxy, $NO_2-$, $R_nN-$ wherein R is independently hydrogen or $C_1$ to $C_5$ alkyl and n=2;

$R_5$ is hydrogen, F, Cl, B, I, $C_1-C_5$ alkyl, a halogen substituted $C_1$ to $C_5$ alkyl, $C_1$ to $C_5$ alkoxy, $NO_2-$, $R_nN-$ wherein R is independently hydrogen or $C_1$ to $C_5$ alkyl and n=2;

$R_6$ is hydrogen, $C_1-C_5$ alkyl, $C_3-C_6$ cyclo alkyl or phenyl;

$R_7$ is hydrogen, $C_1-C_5$ alkyl, alkoxycarbonyl wherein said alkoxy portion is a $C_1-C_5$ alkoxy or a $C_2-C_6$ cycloalkoxy, a phenoxycarbonyl; and $R_8$ is hydrogen, alkoxycarbonyl, as defined above or phenoxycarbonyl which may be substituted with a halogen or alkyl.

3. A method according to claim 1 wherein said ester has the following formula:

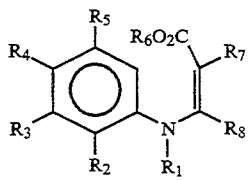

wherein:
$R_1$ is hydrogen; $C_1-C_5$ alkyl; $C_3-C_6$ cycloalkyl; $C_1-C_5$ halo-substituted $C_1$ to $C_5$ alkyl wherein halo is F, Cl, Br or I; aryl or $C_1$ to $C_5$ hydroxyalkyl and, $C_1$ to $C_5$ mercaptoalkyl, $R_1$ together with $R_2$ can be joined with an alkylene, oxyalkylene or thioalkylene group to form a 5 or 6 member heterocyclic ring;

$R_2$ is hydrogen, F, Cl, B, I, $C_1-C_5$ alkyl, halogen substituted $C_1$ to $C_5$ alkyl, $C_1-C_5$ alkoxy, $R_2$ together with $R_1$ can be joined with an alkylene, oxyalkylene or thioalkylene group to form a 5 or 6 member ring;

$R_3$ is F, Cl, B, I, halogen substituted $C_1$ to $C_4$ alkyl, $C_1$ to $C_5$ alkoxy, or $R_2N-$ wherein R is independently hydrogen, or $C_1-C_5$ alkyl;

$R_4$ is F, Cl, B, I, $C_1$ to $C_5$ alkyl;

$R_5$ is hydrogen, halogen (F, Cl, B, I), $C_1-C_5$ alkyl or $NO_2-$;

$R_6$ is hydrogen, $C_1-C_5$ alkyl, $C_3-C_5$ cyclo alkyl or phenyl;

$R_7$ is hydrogen, $C_1-C_5$ alkyl, alkoxycarbonyl wherein said alkoxy portion is a $C_1-C_5$ alkoxy or a $C_2-C_6$ cycloalkoxy or, a phenoxycarbonyl; and $R_8$ is hydrogen, alkoxycarbonyl, as defined above or phenoxycarbonyl which may be substituted with a halogen or alkyl.

4. A method according to claim 2 wherein $R_1$ is a $C_2$ alkyl, $R_2$, $R_3$, and $R_4$ are fluoro and $R_5$ is hydrogen.

5. A method according to claim 2 wherein said heating is conducted at a temperature of about 40°–180° C.

6. A method according to claim 2 wherein said heating is conducted at a temperature of about 60°–150° C.

7. A method according to claim 2 wherein said heating is conducted at a temperature of about 70°–90° C.

8. A method according to claim 2 wherein said reaction medium contains a diluent.

9. A method according to claim 2 wherein $R_1$ is a $C_2$ fluoroalkyl, $R_2$, $R_3$, $R_4$ are fluoro, $R_5$ is hydrogen.

10. A method according to claim 2 wherein $R_1$ is a $C_2$ alkyl, $R_2$ is hydrogen, $R_3$ is chloro, R4 is fluoro and $R_5$ is hydrogen.

11. A method according to claim 2 wherein $R_1$ is a $C_2$ alkyl, $R_2$ is hydrogen, $R_3$ and $R_4$ are fluoro, $R_5$ is hydrogen.

12. A method according to claim 2 wherein $R_1$ is cyclopropyl, $R_2$ is hydrogen, $R_3$ is chloro, $R_4$ is fluoro, $R_5$ is hydrogen.

13. A method according to claim 2 wherein $R_1$ is cyclopropyl, $R_2$ is hydrogen, $R_3$ and $R_4$ are fluoro and $R_5$ is hydrogen.

14. A method according to claim 2 wherein $R_1$ and $R_2$ together are a methyloxyethylene ring, $R_3$, $R_4$ are fluoro and $R_5$ is hydrogen.

15. A method according to claim 2 wherein $R_1$ is cyclopropyl, $R_2$ is methoxy, $R_3$ and $R_4$ are fluoro, and $R_5$ is hydrogen.

16. A method according to claim 2 wherein $R_1$ is cyclopropyl, $R_2$ is hydrogen, $R_3$ and $R_4$ are fluoro, and $R_5$ is methyl.

17. A method according to claim 2 wherein $R_1$ is cyclopropyl, $R_2$ is hydrogen, $R_3$ is chloro, $R_4$ is fluoro, and $R_5$ is methyl.

18. A method according to claim 2 wherein $R_1$ is cyclopropyl, $R_2$, $R_3$ and $R_4$ are fluoro, and $R_5$ is nitro.

19. A method according to claim 2 wherein $R_1$ and $R_2$ together are fluoromethyl-oxyalkylene ring, $R_3$ and $R_4$ are fluoro, and $R_5$ is hydrogen.

20. A method according to claim 2 wherein $R_1$ and $R_2$ together are a thioalkylene ring, $R_3$ and $R_4$ are fluoro and $R_5$ is hydrogen.

* * * * *